United States Patent [19]
Lee et al.

[11] Patent Number: 5,767,063
[45] Date of Patent: Jun. 16, 1998

[54] HUMAN IL-8 RECEPTOR AND ANTIBODIES THERETO

[75] Inventors: James Lee, San Bruno; William E. Holmes, Pacifica; William I. Wood, San Mateo, all of Calif.

[73] Assignee: Genentech, Inc., San Francisco, Calif.

[21] Appl. No.: 410,453

[22] Filed: Mar. 24, 1995

Related U.S. Application Data

[62] Division of Ser. No. 234,494, Apr. 28, 1994, abandoned, which is a continuation of Ser. No. 677,211, Mar. 29, 1991, abandoned.

[51] Int. Cl.$^6$ .................. C07K 14/715; C07K 16/28
[52] U.S. Cl. ........................... 514/2; 514/8; 514/12; 530/350; 530/387.7; 530/387.9; 530/388.22; 435/69.1; 435/69.4
[58] Field of Search ................ 530/350, 387.9, 530/387.1, 388.22; 514/2, 8, 12; 435/69.1, 69.7

[56] References Cited

U.S. PATENT DOCUMENTS

| | | | |
|---|---|---|---|
| 5,374,506 | 12/1994 | Murphy | 530/350 |
| 5,543,503 | 8/1996 | Chundharapai et al. | 530/388.22 |

FOREIGN PATENT DOCUMENTS

| | | |
|---|---|---|
| WO 92/17497 | 10/1992 | WIPO |
| WO 92/18641 | 10/1992 | WIPO |
| WO 93/06229 | 4/1993 | WIPO |

OTHER PUBLICATIONS

Beckman et al., "Molecular characterization of the interleukin–8 receptor" *Biochem. & Biophys. Res. Comm.* 179(2): 784–789 (Sep. 16, 1991).

Besemer et al., "Specific Binding, Internalization, and Degradation of Human Neutrophil Activating Factor by Human Neutrophil Activating Factor by Human Polymorphonuclear Leukocytes" *Journal of Biological Chemistry* 264:17409–17415 (1989).

Boulay et al., "Synthesis and use of a novel N–formyl peptide derivatives to isolate a human N–formyl peptide receptor cDNA" *Biochem. Biophys Res. Comm.* 168(3):1103–1109 (1990).

Chuntharapai et al., "Generation of characterization of monoclonal antibodies (mAbs) to human IL 8 receptor A" *J. Immunol.* (abstract #708) 150(8(2)):126A (Apr. 1993).

Chuntharapai et al., "Neutralizing monoclonal antibodies to human IL–8 receptor A map to the NH$_2$–terminal region of the receptor" *J. Immunl.* 152(4):1783–1789.

D'Andrea et al., "Expression Cloning of the Murine Erythropoietin Receptor" *Cell* 57:277–285 (1989).

Gayle III et al., "Importance of the Amino Terminus of the Interleukin–8 Receptor in Ligand Interactions" *Journal of Biological Chemistry* 268(10):7283–7289 (1993).

Gerard & Gerard, "The chemotactic receptor for human C5a anaphylatoxin" *Nature* 349:614–617 (1991).

Grob et al., "Characterization of a Receptor for Human Monocyte–derived Neutrophil Chemotacic Factor/Interleukin–8" *Journal of Biological Chemistry* 265(14):8311–8316 (1990).

Hammond et al., "Generation of neutralizing antibodies to human interleukin–8 (IL8) receptors" *J. Cell Biochem.* (Suppl. 18B) 318:Abstract #0108 (1994).

Hebert et al., "Partial functional mapping of the human interleukin–8 type A receptor" *Journal of Biological Chemistry* 268(25):18549–18553 (1993).

Holmes et al., "Structure and functional expression of a human interleukin–8 receptor" *Science* 253(5025):1278–1280 (Sep. 13, 1991).

LaRosa et al., "Amino terminus of the interleukin–8 receptor is a major determinant of receptor subtype specificity" *Journal of Biological Chemistry* 267(35):25402–25406 (1992).

Lee et al., "Characterization of Two High Affinity Human Interleukin–8 Receptors" *Journal of Biological Chemistry* 267(23):16283–16287 (1992).

Murphy and Tiffany, "Cloning of complementary DNA encoding a functional human interleukin–8 receptor" *Science* 253(5025):1280–1283 (Sep. 13, 1991).

Ramachandran et al., "The Structural and Functional Interrelationships of Muscarinic Acetylcholine Receptor Subtypes" *Bioessays* 10:54–57 (1989).

Samanta et al., "Identification and characterization of specific receptors for monocyte–derived neutrophil chemotactic factor (MDNCF) on human neutrophils" *Journal of Experimental Medicine* 169:1185–1189 (1989).

Saragovi et al., "The Murine Interleukin 2 Receptor: Irreversible Cross–Linking of Radiolabled Interleukin 2 to High Affintiy Interleukin 2 Receptors Reveals a Noncovalently Associated Subunit" *J. Immunol.* 139(6):1918–1926 (Sep. 15, 1987).

Sims et al., "cDNA Expression Cloning of the II–1 Receptor, a Member of the Immunoglobulin Superfamily" *Science* 241:585–589 (1988).

Thomas et al., "The Interleukin–8 Receptor Is Encoded by a Neutrophil–specific cDNA clone, F3R" *Journal of Biological Chemistry* 266(23):14839–14841 (1991).

Thomas et al., "Molecular cloning of the fMet–Leu–Phe receptor from neutropils" *Journal of Biological Chemistry* (published erratum appears in J Biol Chem 1992 Jul. 5;267 (19):13780) 265 (33):20061–20064 (Nov. 25, 1990).

Ye et al., "Inhibition of IL–8 binding to the type B IL–8 receptor by an anti–II–8 receptor antibody" *FASEB J.* (Abstract #786) 8(4–5) :A136 (1994).

Quan, J.M. et al., "Antibodies against the N–terminus of IL–8 receptor A inhibit neutrophil chemotaxis" *Biochem. & Biophys. Res. Comm.* 219:405–411 (1996).

Primary Examiner—John Ulm
Assistant Examiner—Prema Mertz
Attorney, Agent, or Firm—Richard B. Love

[57] ABSTRACT

The cDNA encoding a member of or a class of novel PF4A receptors has been identified in human tissue. Provided herein is nucleic acid sequence of a PF4A receptor (the IL-8 receptor) useful as a diagnostic and in the recombinant preparation of PF4A receptors. The PF4A receptor is used in the preparation and purification of antibodies capable of binding to the receptor, and in diagnostic assays.

7 Claims, 12 Drawing Sheets

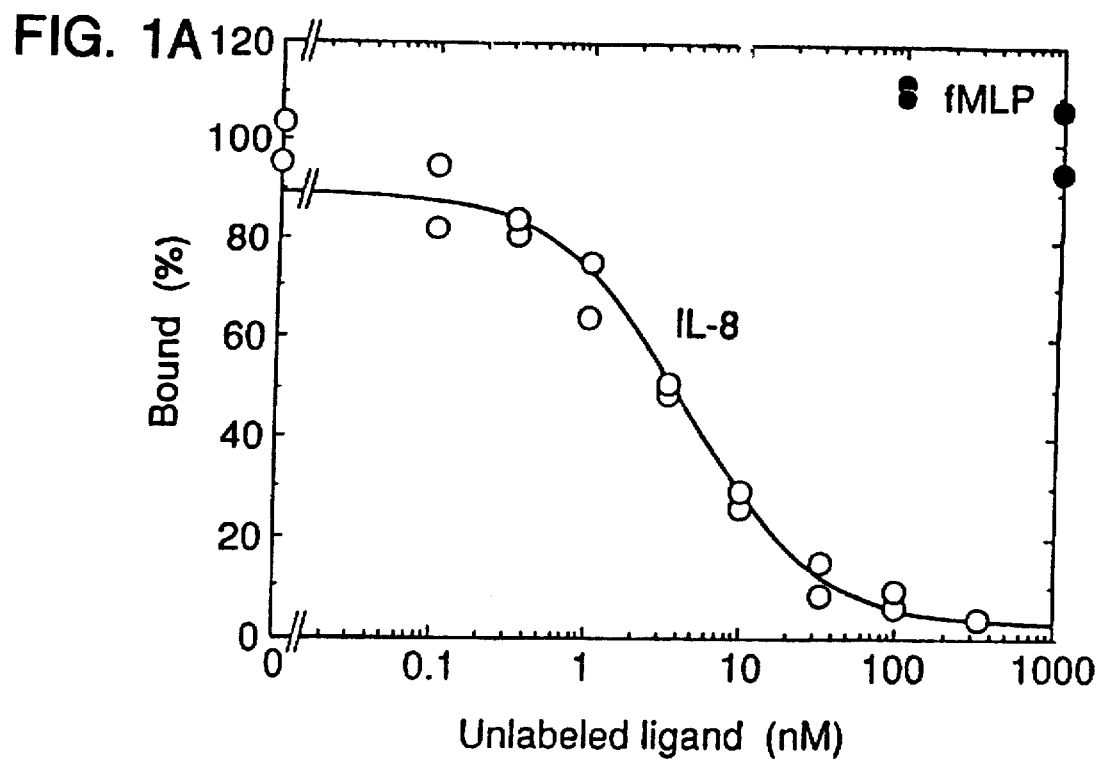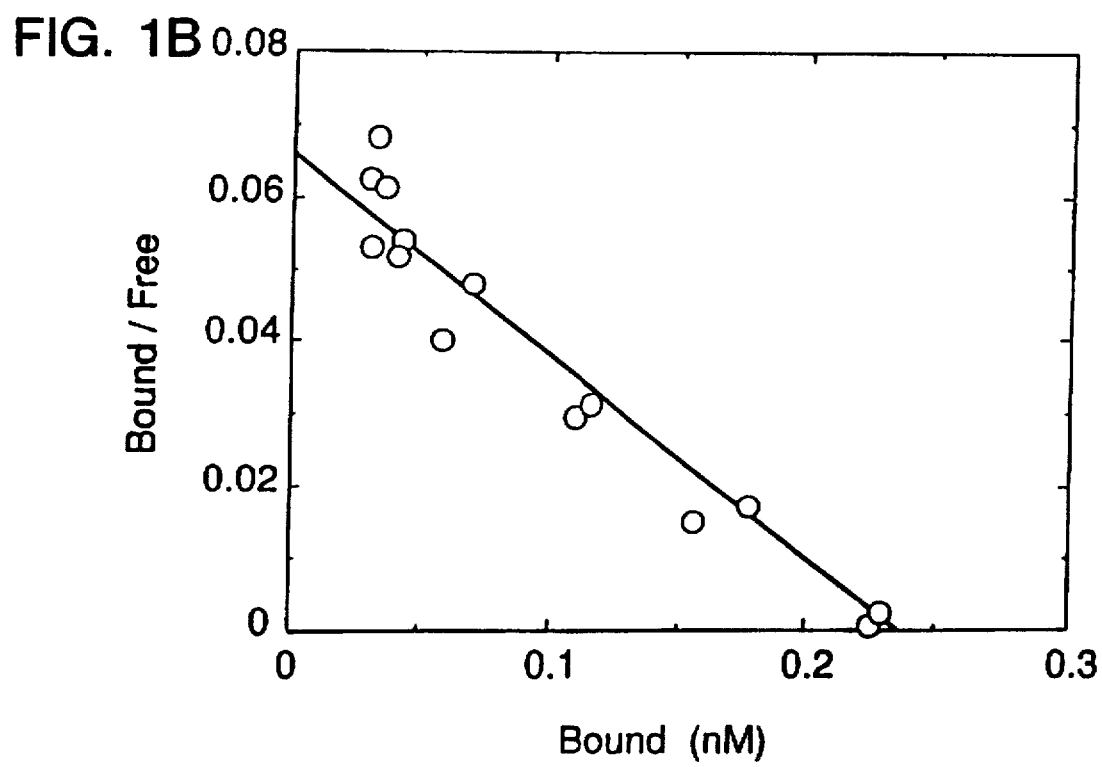

CCTGGCCGGT GCTTCAGTTA GATCAAACCA TTGCTGAAAC TGAAGAGGAC 50

ATG TCA AAT ATT ACA GAT CCA CAG ATG TGG GAT TTT 86
Met Ser Asn Ile Thr Asp Pro Gln Met Trp Asp Phe
1                 5                   10

GAT GAT CTA AAT TTC ACT GGC ATG CCA CCT GCA GAT GAA 125
Asp Asp Leu Asn Phe Thr Gly Met Pro Pro Ala Asp Glu
       15                  20                  25

GAT TAC AGC CCC TGT ATG CTA GAA ACT GAG ACA CTC AAC 164
Asp Tyr Ser Pro Cys Met Leu Glu Thr Glu Thr Leu Asn
            30                  35

AAG TAT GTT GTG ATC ATC GCC TAT GCC CTA GTG TTC CTG 203
Lys Tyr Val Val Ile Ile Ala Tyr Ala Leu Val Phe Leu
    40                  45                  50

FIG. 2A

TM1
CTG AGC CTG CTG GGA AAC TCC CTG ATG CTG GTG ATC 242
Leu Ser Leu Leu Gly Asn Ser Leu Met Leu Val Ile
             55                    60

TTA TAC AGC AGG GTC GGC CGC TCC GTC ACT GAT GTC TAC 281
Leu Tyr Ser Arg Val Gly Arg Ser Val Thr Asp Val Tyr
         65                  70                  75
                                              TM2

CTG CTG AAC CTG GCC GAC CTA CTC TTT GCC CTG 320
Leu Leu Asn Leu Ala Asp Leu Leu Phe Ala Leu
             80                  85         90

ACC TTG CCC ATC TGG GCC GCC TCC AAG GTG AAT GGC TGG 359
Thr Leu Pro Ile Trp Ala Ala Ser Lys Val Asn Gly Trp
             95                  100

FIG. 2B

```
ATT TTT GGC ACA TTC CTG TGC AAG GTG GTC TCA CTC CTG  398
Ile Phe Gly Thr Phe Leu Cys Lys Val Val Ser Leu Leu
    105                         110                115
                                              TM3

AAG GAA GTC AAC TTC TAC AGT GGC ATC CTG CTG TTG GCC  437
Lys Glu Val Asn Phe Tyr Ser Gly Ile Leu Leu Leu Ala
                    120                 125

TGC ATC AGT GTG GAC CGT TAC CTG GCC ATT GTC CAT GCC  476
Cys Ile Ser Val Asp Arg Tyr Leu Ala Ile Val His Ala
130                     135                 140

ACA CGC ACA CTG ACC CAG AAG CGT CAC TTG GTC AAG TTT  515
Thr Arg Thr Leu Thr Gln Lys Arg His Leu Val Lys Phe
            145                 150                155
                                                TM4

GTT TGT CTT GGC TGG GGA CTG TCT ATG AAT CTG TCC      554
Val Cys Leu Gly Trp Gly Leu Ser Met Asn Leu Ser
                160                 165
```

FIG. 2C

```
CTG CCC TTC TTC CTT TTC CGC CAG GCT TAC CAT CCA AAC  593
Leu Pro Phe Phe Leu Phe Arg Gln Ala Tyr His Pro Asn
        170                 175                 180

AAT TCC AGT CCA GTT TGC TAT GAG GTC CTG GGA AAT GAC  632
Asn Ser Ser Pro Val Cys Tyr Glu Val Leu Gly Asn Asp
             185                 190

ACA GCA AAA TGG CGG ATG GTG TTG CGG ATC CTG CCT CAC  671
Thr Ala Lys Trp Arg Met Val Leu Arg Ile Leu Pro His
    195                 200                 205
                                        TM5

ACC TTT GGC TTC ATC GTG CCG CTG TTT GTC ATG CTG TTC  710
Thr Phe Gly Phe Ile Val Pro Leu Phe Val Met Leu Phe
        210                 215                 220
```

FIG. 2D

```
TGC TAT GGA TTC ACC CTG CGT ACA CTG TTT AAG GCC CAC  749
Cys Tyr Gly Phe Thr Leu Arg Thr Leu Phe Lys Ala His
                225                 230

ATG GGG CAG AAG CAC CGA GCC ATG AGG GTC ATC TTT GCT  788
Met Gly Gln Lys His Arg Ala Met Arg Val Ile Phe Ala
        235                 240              245
                                            TM6

GTC GTC CTC ATC TTC CTG CTT TGC TGG CTG CCC TAC AAC  827
Val Val Leu Ile Phe Leu Leu Cys Trp Leu Pro Tyr Asn
    250                 255

CTG GTC CTG CTG GCA GAC ACC CTC ATG AGG ACC CAG GTG  866
Leu Val Leu Leu Ala Asp Thr Leu Met Arg Thr Gln Val
260                 265                 270

ATC CAG GAG ACC TGT GAG CGC CGC AAC AAC ATC GGC CGG  905
Ile Gln Glu Thr Cys Glu Arg Arg Asn Asn Ile Gly Arg
        275                 280                 285
```

FIG. 2E

```
GCC CTG GAT GCC ACT GAG ATT CTG GGA TTT CTC CAT AGC   944
Ala Leu Asp Ala Thr Glu Ile Leu Gly Phe Leu His Ser
300                 290                 295

TM7
TGC CTC AAC CCC ATC ATC TAC GCC TTC ATC GGC CAA AAT   983
Cys Leu Asn Pro Ile Ile Tyr Ala Phe Ile Gly Gln Asn
                300                 305           310

TTT CGC CAT GGA TTC CTC AAG ATC CTG GCT ATG CAT GGC  1022
Phe Arg His Gly Phe Leu Lys Ile Leu Ala Met His Gly
        315                 320

CTG GTC AGC AAG GAG TTC TTG GCA CGT CAT CGT GTT ACC  1061
Leu Val Ser Lys Glu Phe Leu Ala Arg His Arg Val Thr
325                 330                 335

TCC TAC ACT TCT TCG TCT GTC AAT GTC TCT TCC AAC CTC  1100
Ser Tyr Thr Ser Ser Ser Val Asn Val Ser Ser Asn Leu
        340                 345                 350

FIG. 2F
```

| | | | |
|---|---|---|---|
| TGAAACCAT | CGATGAAGGA | ATATCTCTTC | TCAGAAGGAA | AGAATAACCA 1150 |
| ACACCCTGAG | GTTGTGTGTG | GAAGGTGATC | TGGCTCTGGA | CAGGCACTAT 1200 |
| CTGGGTTTTG | GGGGACGCT | ATAGGATGTG | GGGAAGTTAG | GAACTGGTGT 1250 |
| CTTCAGGGGC | CACACCAACC | TTCTGAGGAG | CTGTTGAGGT | ACCTCCAAGG 1300 |
| ACCGGCCTTT | GCACCTCCAT | GGAAACGAAG | CACCATCATT | CCCGTTGAAC 1350 |
| GTCACATCTT | TAACCCACTA | ACTGGCTAAT | TAGCATGGCC | ACATCTGAGC 1400 |
| CCCGAATCTG | ACATTAGATG | AGAGAACAGG | GCTGAAGCTG | TGTCCTCATG 1450 |

FIG. 2G

```
AGGGCTGGAT GCTCTCGTTG ACCCTCACAG GAGCATCTCC TCAACTCTGA 1500
GTGTTAAGCG TTGAGCCACC AAGCTGGTGG CTCTGTGTGC TCTGATCCGA 1550
GCTCAGGGGG GTGGTTTTCC CATCTCAGGT GTGTTGCAGT GTCTGCTGGA 1600
GACATTGAGG CAGGCACTGC CAAAACATCA ACCTGCCAGC TGGCCTTGTG 1650
AGGAGCTGGA AACACATGTT CCCCTTGGGG GTGGTGGATG AACAAAGAGA 1700
AAGAGGGTTT GGAAGCCAGA TCTATGCCAC AAGAACCCCC TTTACCCCCA 1750
```

FIG. 2H

```
TGACCAACAT CGCAGACACA TGTGCTGGCC ACCTGCTGAG CCCCAAGTGG 1800
AACGAGACAA GCAGCCCTTA GCCCTTCCCC TCTGCAGCTT CCAGGCTGGC 1850
GTGCAGCATC AGCATCCCTA GAAAGCCATG TGCAGCCACC AGTCCATTGG 1900
GCAGGCAGAT GTTCCTAATA AAGCTTCTGT TCC 1933
```

FIG. 2I

HUMAN IL-8 RECEPTOR AND ANTIBODIES THERETO

This is a divisional of application Ser. No. 08/234,494 filed on 28 Apr. 1994 now abandoned, which is a continuation of Ser. No. 07/677,211, filed on 29 Mar. 1991, now abandoned.

This invention relates to the field of assaying platelet actor 4 neutrophil agonists (hereafter "PF4A") and the preparation of agonists and antagonists to the members of this family.

BACKGROUND OF THE INVENTION

While interleukin-8 was initially identified as a chemoattractant for neutrophils, and was known to bind a receptor on neutrophils[8-10] it has in addition a wide range of pro-inflammatory activities including the stimulation of degranulation and the upregulation of the cell adhesion molecule MAC-1 and of the complement receptor CR1[1]. IL-8 can also mediate the inhibition of the adherence of neutrophils to activated endothelial cells[2].

IL-8 is a member of a family of ten or more pro-inflammatory cytokines with an $M_r \sim 10,000$[1]. This larger family of proteins is called the platelet factor 4 superfamily (Wolpe et al., "FASEB J." 3:2565-73 [1989]). Some members of the platelet factor 4 superfamily, in general the subset referred to as CXC peptides (including IL-8), possess neutrophil agonist activity, e.g. NAP-2, MIP-2 and NAP-3 (MGSA/gro), and are referred to as "PF4A" herein.

It is an object of this invention to identify receptors for the pF4A family.

It is another object of this invention to obtain DNA encoding these receptors, and to express them in host cells.

It is an additional object of this invention to provide isolates of pF4A receptors for diagnostic and therapeutic purposes.

A still further object is to prepare variants of such receptors for therapeutic purposes or for purification of pF4A family members.

These and other objects of this invention will be apparent from the specification as a whole.

SUMMARY OF THE INVENTION

These objects are accomplished, in one aspect, by providing an isolated novel PF4A receptor polypeptide, including polypeptides that are related structurally to PF4A receptor. Members of this class of polypeptide are hereafter termed PF4A receptor, and include N-terminal fragments thereof.

In another aspect, the invention provides a composition comprising the PF4A receptor that is free of contaminating polypeptides of the animal species from which the PF4A receptor is derived.

The PF4A receptor or fragments thereof (which also may be synthesized by chemical methods) are fused (by recombinant expression or in vitro covalent methods) to an immunogenic polypeptide and this fusion polypeptide, in turn, is used to immunize an animal to raise antibodies against a PF4A receptor epitope. Anti-PF4A receptor antibodies are recovered from the serum of immunized animals. Alternatively, monoclonal antibodies are prepared from cells of the immunized animal in conventional fashion.

Immobilized anti-PF4A receptor antibodies are useful particularly in the diagnosis (in vitro or in vivo) or purification of the PF4A receptor.

Substitutional, deletional, or insertional variants of the PF4A receptor are prepared by in vitro or recombinant methods and screened for immuno-crossreactivity with the PF4A receptor and for PF4A receptor antagonist or agonist activity.

The PF4A receptor also is derivatized in vitro to prepare immobilized PF4A receptor and labeled PF4A receptor, particularly for purposes of diagnosis of PF4A receptor or its antibodies, or for affinity purification of PF4A receptor antibodies.

The PF4A receptor, its derivatives, or its antibodies are formulated into physiologically acceptable vehicles, especially for therapeutic use. Such vehicles include sustained-release formulations of the PF4A receptor.

In still other aspects, the invention provides an isolated nucleic acid molecule encoding the PF4A receptor, labeled or unlabeled, and a nucleic acid sequence that is complementary, or hybridizes under stringent conditions to, a nucleic acid sequence encoding the PF4A receptor.

In addition, the invention provides a replicable vector comprising the nucleic acid molecule encoding the PF4A receptor operable linked to control sequences recognized by a host transformed by the vector; host cells transformed with the vector; and a method of using a nucleic acid molecule encoding the PF4A receptor to effect the production of PF4A receptor, comprising expressing the nucleic acid molecule in a culture of the transformed host cells and recovering the PF4A receptor from the host cell culture. The nucleic acid sequence is also useful in hybridization assays for PF4A receptor nucleic acid. The recombinant host cells are particularly useful in assaying the appropriate pF4A members.

In further embodiments, the invention provides a method for producing PF4A receptor comprising inserting into the DNA of a cell containing the nucleic acid encoding the PF4A receptor a transcription modulatory element in sufficient proximity and orientation to the PF4A receptor nucleic acid to influence transcription thereof, with an optional further step comprising culturing the cell containing the transcription modulatory element and the PF4A receptor nucleic acid.

In still further embodiments, the invention provides a cell comprising the nucleic acid encoding the PF4A receptor and an exogenous transcription modulatory element in sufficient proximity and orientation to the PF4A receptor nucleic acid to influence transcription thereof; and a host cell containing the nucleic acid encoding the PF4A receptor operably linked to exogenous control sequences recognized by the host cell.

Still further is provided a method for obtaining cells having increased or decreased transcription of the nucleic acid encoding the PF4A receptor comprising:

(a) providing cells containing the PF4A receptor nucleic acid;

(b) introducing into the cells a transcription modulating element; and (c) screening the cells for a cell in which the transcription of the PF4A receptor nucleic acid is increased or decreased.

BRIEF DESCRIPTION OF THE DRAWINGS

FIG. 1 depicts the high affinity binding of IL-8 to COS cells transfected with clone pRK5B.il8r1.1. a, Competition with unlabelled IL-8 or fMLP. b, Scatchard analysis of the IL-8 competition data; apparent Kd=3.6 nM, average of 820,000 binding sites/cell. Similar competitions with human neutrophils gave Kd=1.1 nM, 31000 binding sites/cell.

FIGS. 2A–2I depict the amino acid (SEQ ID NO:1) and nucleotide (SEQ ID NO:2) sequences of the IL-8 receptor cDNA insert from clone pRK5B.il8r1.1. The seven putative transmembrane domains are shown. There are 4 extracellular segments and 4 intracellular segments, each being separated by one of the transmembrane domains. The extracellular segments are approximately delineated by residues 1–39, 99–111, 134–154, 175–203 and 265–290. The IL-8 receptor contains 3 potential N-linked glycosylation sites in the first extracellular region and 3 more in the third extracellular loop.

DETAILED DESCRIPTION OF THE INVENTION

Figure 3A:
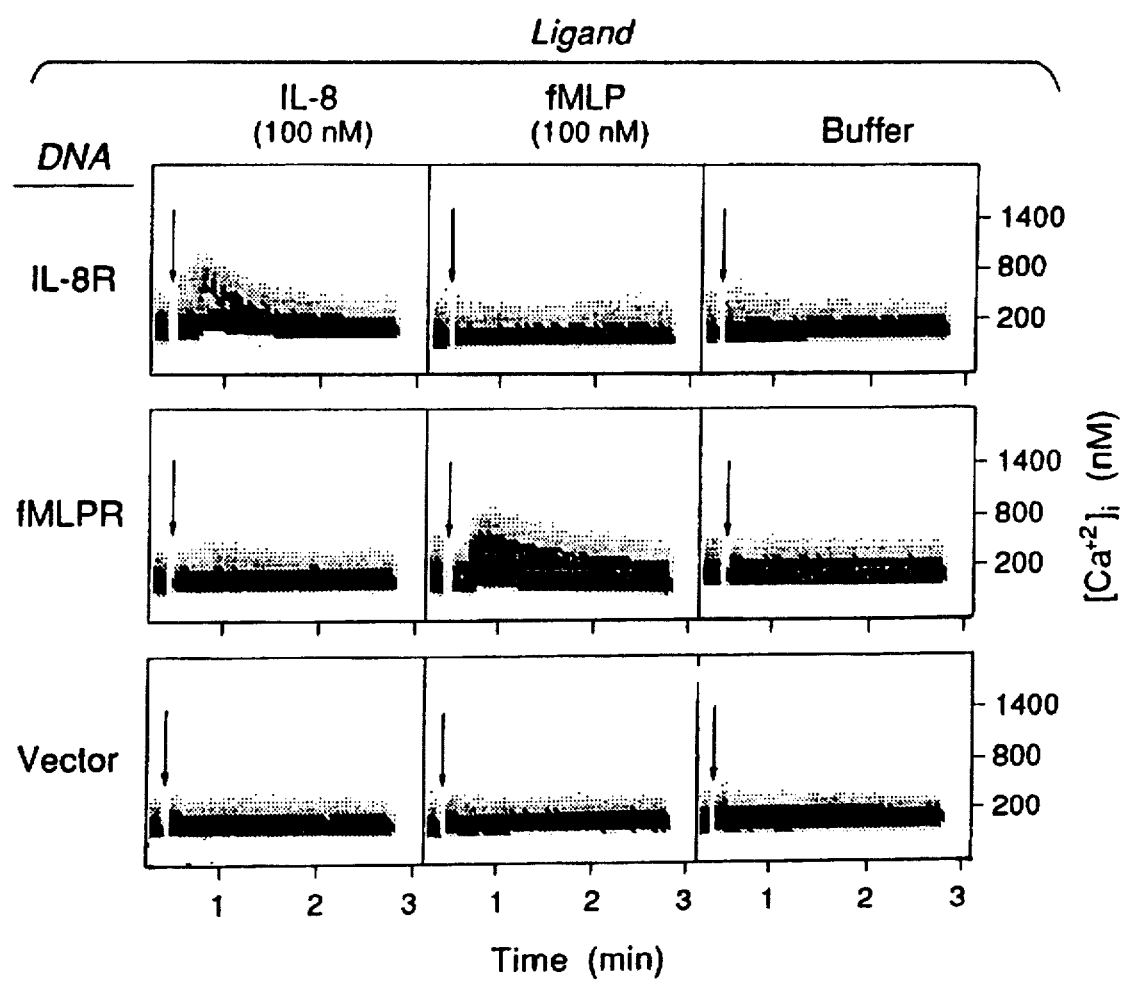
FIG. 3a depicts the flow cytometry determination of the intracellular $Ca^{++}$ response of transfected human IL-8 and fMLP receptors to their ligands. Human embryonic kidney 293 cells were transfected by electroporation[19] with IL-8 receptor (clone pRK5B.il8r1.1), fMLP receptor (human fMLP receptor cDNA[3] in the vector pRK5), or vector (pRK5B[18]) DNA. After two days, the cells were loaded with 2 μM indo-1 acetoxymethyl ester in RPMI medium for 30 min at 37°. Intracellular $Ca^{++}$ was measured with a Coulter 753 flow cytometer using the ratio of 405 and 525 nm fluorescence[23].
Figure 3B:
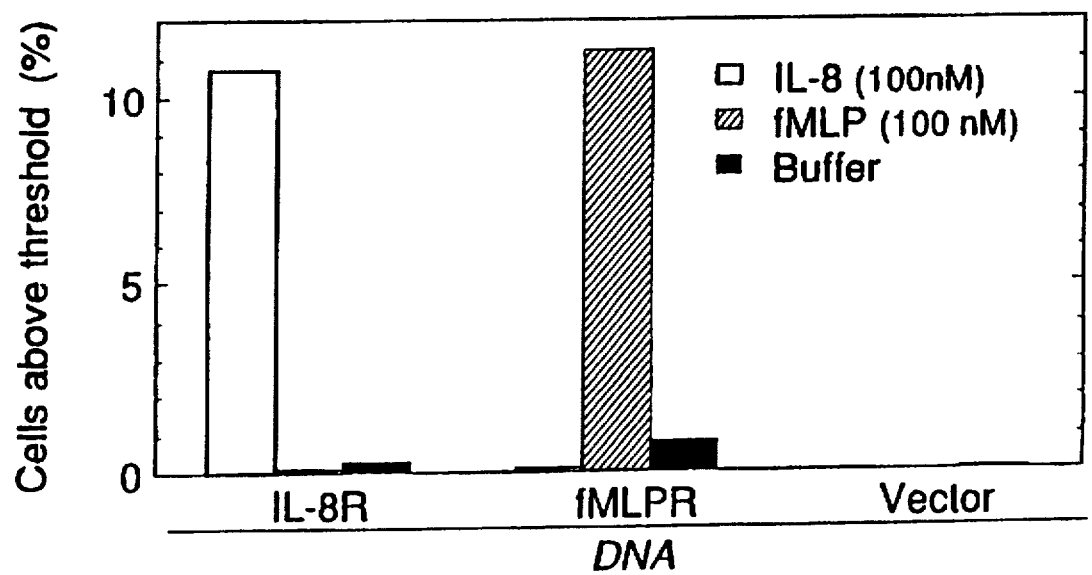
FIG. 3b illustrates the percent of cells above 400 nM $Ca_i^{++}$ for the time period after addition of IL-8 (about 15 sec. into each run).

We have isolated by expression cloning a cDNA encoding the human neutrophil IL-8 receptor. The amino acid sequence shows that it is a member of the G-protein coupled receptor family with clear similarity (29% amino acid identity) to the human neutrophil receptors for the chemoattractants f-Met-Leu-Phe[3] and C5a[4]. Although the sequence may be the human homologue of what has been identified as the an isoform of the rabbit f-Met-Leu-Phe receptor[5], we show that when transfected into mammalian cells, this receptor clone confers high affinity binding to IL-8 and produces a transient $Ca^{++}$ mobilization in response to IL-8 with no binding or response to f-Met-Leu-Phe.

A COS cell expression cloning strategy[6,7] was used to isolate clones encoding the IL-8 receptor. A cDNA library constructed from human neutrophil mRNA in the mammalian expression vector pRK5B was transfected into COS-7 cells as pools of 2500 clones, and the cells screened for the binding of $^{125}$I-IL-8. One positive pool from the first 58 transfections was partitioned into smaller pools until a pure clone (pRK5B.il8r1.1) was obtained. FIG. 1 shows the competition of $^{125}$I-IL-8 binding by unlabelled IL-8 to COS cells transfected with the isolated clone. Analysis of this data gives a Kd of 3.6 nM for IL-8 binding which is within the range of 0.8 to 4 nM reported for IL-8 binding to human neutrophils[8–10]. There is no competition of the IL-8 binding by the chemotactic peptide f-Met-Leu-Phe (fMLP).

The DNA sequence of the isolated cDNA clone FIGS. 2A–2I (SEQ ID NO:2) contains a single long open reading frame beginning with a methionine residue that matches the consensus expected for a translation initiation site[11]. This open reading frame encodes a protein of 350 amino acids (translated $M_r$ 39.5 kD). The amino acid sequence shares several features with the G-protein coupled receptors of the rhodopsin superfamily including seven hydrophobic domains that are presumed to span the cell membrane and N-linked glycosylation sites near the N-terminus[12] (see below).

The encoded amino acid sequence is the most similar to a recently cloned sequence for the rabbit fMLP receptor[5]. The similarity is sufficiently high (79% amino acid identity overall with multiple stretches of more than 20 contiguous amino acid matches) that these two sequences may well be species homologs of the same receptor. The human fMLP receptor has also been cloned[3]; it has only 26% amino acid identity with the rabbit fMLP receptor (and 29% identity to the human IL-8 receptor presented here). The considerable divergence between the rabbit and human fMLP receptor amino acid sequences has lead to the suggestion in the art (now believed to be possibly erroneous) that these may be two isoforms of the fMLP receptor[5].

Neutrophils respond to the chemoattractants IL-8 and fMLP with a rapid, transient increase in the intracellular free $Ca^{30+}$ concentration[1,13]. In order to verify the identification of the clone isolated here as the IL-8 receptor, we have determined the intracellular $Ca^{++}$ response of transfected cells to added IL-8 as well as fMLP. We have used parallel experiments with transfected human fMLP receptor or with the expression vector as controls. Flow cytometer analysis shows a clear transient increase in intracellular $Ca^{++}$ for the transfected IL-8 receptor in response to IL-8. No response is found to fMLP. Conversely, cells transfected with the human fMLP receptor respond to fMLP but not to IL-8. No response to either chemoattractant is found in vector transfected cells. Only a subset of the cells are expected to respond in these experiments as the transfection efficiency is estimated to be 15–25%. Binding experiments[14] also failed to detect any binding of $^3$H-fMLP to the expressed IL-8 receptor or $^{125}$I-IL-8 to the expressed human fMLP receptor. These experiments clearly demonstrate the specificity of the two receptors for their respective ligands; a result expected based on the lack of binding competition between IL-8 and fMLP for neutrophils[1]. These results also demonstrate that the cloned receptors function in second message signaling in response to ligand binding.

Blot hybridization of the cloned IL-8 receptor cDNA to human neutrophil mRNA, shows strong bands of 2.4 and 3.0 kb as well as a fainter band at 3.5 kb. While it is clear from the DNA sequence data presented in FIG. 2 (SEQ ID NO.1) that the mRNA for the receptor has a long 3' untranslated region, additional work will be needed to establish whether the multiple RNA bands are due to multiple polyadenylation sites. No hybridization was detected to mRNA from U266 or Jurkat cell lines, which are of the B cell and T cell lineages. No hybridization was found for mRNA from the monocyte cell line U937 as well, in spite of the reports of low levels of IL-8 binding to these cells[9,10].

Alignment of the receptor sequences for the three neutrophil chemoattractants IL-8, fMLP[3], and C5a[4] shows that they form a subfamily of the G-protein coupled receptors with 29–34% amino acid identity. This subfamily has a short third intracellular loop as compared with other G-protein coupled receptors such as the β-adrenergic[12] or muscarinic acetylcholine receptors[15]. This loop contains determinants at least partially responsible for the binding of G-proteins to the receptors[12]. The intracellular C-terminal region of the IL-8 receptor, while not very similar to that of the fMLP and C5a receptors does preserve a high number of serine and threonine residues that may function as phosphorylation sites. As has been noted for the C5a receptor[4], the N-terminal extracellular region for the IL-8 receptor has several acidic residues. These may aid in the binding of IL-8 which is quite basic (p~9.5).

I. DEFINITIONS

In general, the following words or phrases have the indicated definition when used in the description, examples, and claims:

The term "PF4A receptor" is defined as a polypeptide having a qualitative biological activity in common with the PF4A receptor of or FIGS. 2A-2I (SEQ ID NO.1), and which has at least 75% amino acid sequence identity with the PF4A receptor of FIGS. 2A-2I (SEQ ID NO.1).

Included within the scope of the PF4A receptor as that term is used herein are PF4A receptors having the translated presequence or translated mature amino acid sequences of the human PF4A receptors as set forth in FIGS. 2A-2I (SEQ ID NO.1), deglycosylated or unglycosylated derivative of the PF4A receptor, homologous amino acid sequence variants of the sequence of FIGS. 2A-2I (SEQ ID NO.1), and homologous in vitro-generated variants and derivatives of the PF4A receptor, which are capable of exhibiting a biological activity in common with the PF4A receptor of FIGS. 2A-2I (SEQ ID NO.1). While native PF4A receptor is a membrane-bound polypeptide, soluble fragments of the PF4A receptor consisting essentially of the extracellular segments of the IL-8 or PF4A receptors are also included within this definition.

Also included within the scope of the term "PF4A receptor" is a polypeptide or protein encoded by the human PF4A receptor nucleotide sequence set forth in FIGS. 2A-2I (SEQ ID NO.1); fragments thereof having at least 15 and preferably at least 30 amino acid residues; fragments thereof having greater than about 5 residues comprising an immune epitope or other biologically active site of the PF4A receptor; amino acid sequence variants of said FIGS. 2A-2I (SEQ ID NO.1) sequence wherein an amino acid residue has been inserted N- or C-terminal to, or within, said FIGS. 2A-2I (SEQ ID NO.1) sequence or its fragment as defined above; and/or amino acid sequence variants of said FIGS. 2A-2I (SEQ ID NO.1) sequence or its fragment as defined above wherein an amino acid residue of said FIGS. 2A-2I (SEQ ID NO.1) sequence or fragment thereof has been substituted by another residue, including predetermined mutations; animal species of the PF4A receptor such as rabbit, rat, porcine, non-human primate, equine, murine, and ovine PF4A receptor and alleles and other naturally occurring variants of the foregoing and human sequences; and derivatives of the PF4A receptor or its fragments as defined above wherein the PF4A receptor or its fragments have been covalently modified by substitution, chemical, enzymatic, or other appropriate means, with a moiety other than a naturally occurring amino acid. The term "PF4A receptor" excludes any polypeptide heretofore identified, including the rabbit MLP receptor[5], or any known polypeptide fragment having the amino acid sequence of PF4A receptor fragments. PF4A receptor amino acid sequence variants generally will share at least about 80%, more preferably >85% sequence identity with the translated sequence shown in FIGS. 2A-2I (SEQ ID NO.1).

Identity or homology with respect to a PF4A receptor in defined herein as the percentage of amino acid residues in the candidate sequence that are identical with the residues in FIGS. 2A-2I (SEQ ID NO.1), after aligning the sequences and introducing gaps, if necessary, to achieve the maximum percent homology, and not considering any conservative substitutions as part of the sequence identity. No N- nor C-terminal extensions, deletions nor insertions shall be construed as reducing identity or homology.

PF4A receptor qualitative biological activity is defined as either 1) immunological cross-reactivity with at least one epitope of a PF4A receptor, including the IL-8 receptor 2) the ability to specifically bind to a PF4A.

Immunologically cross-reactive as used herein means that the candidate polypeptide is capable of competitively inhibiting the binding of a PF4A receptor to polyclonal antibodies or antisera raised against the PF4A receptor. Such antibodies and antisera are prepared in conventional fashion by injecting an animal such as a goat or rabbit, for example, subcutaneously with the known native PF4A receptor in complete Freund's adjuvant, followed by booster intraperitoneal or subcutaneous injection in incomplete Freund's.

The preferred PF4A receptor is the human IL-8 receptor.

"Isolated" PF4A receptor nucleic acid or polypeptide is a PF4A receptor nucleic acid or polypeptide that is identified and separated from at least one contaminant (nucleic acid or polypeptide respectively) with which it is ordinarily associated in nature, such as from the animal or human source of the PF4A receptor nucleic acid or polypeptide. In preferred embodiments, the PF4A receptor will be isolated to pharmaceutically acceptable levels of purity with respect to proteins of its species of origin. The nucleic acid or polypeptide may be labeled for diagnostic and probe purposes, using a label as described and defined further below in the discussion of diagnostic assays.

PF4A receptor "nucleic acid" is defined as RNA or DNA containing greater than ten (10) bases that encodes a PF4A receptor, is complementary to nucleic acid sequence encoding the PF4A receptor, hybridizes to such nucleic acid and remains stably bound to it under stringent conditions, or encodes a polypeptide sharing at least 75% sequence identity, preferably at least 80%, and more preferably at least 85%, with the translated amino acid sequence shown in FIGS. 2A-2I (SEQ ID NO.1). Preferably the DNA which hybridizes to the nucleic acid of FIGS. 2A-2I (SEQ ID NO:2) contains at least 20, more preferably 40, and even more preferably 60 bases. Most preferably, the hybridizing DNA or RNA contains 45 or even more preferably 90 bases. Such hybridizing or complementary nucleic acid, however, is defined further as being novel and unobvious over any prior art nucleic acid including that which encodes, hybridizes under stringent conditions, or is complementary to nucleic acid encoding rabbit fMLP receptor[5].

"Stringent conditions" are any of those that (1) employ low ionic strength and high temperature for washing, for example, 0.015M NaCl/0.0015M sodium citrate/0.1% NaDodSO$_4$ at 50° C.; (2) employ during hybridization 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ hybridization with 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretary leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Plasmids are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

Restriction enzyme digestion of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al. (*Molecular Cloning: A Laboratory Manual* New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103–6114 (1981), and Goeddel et al., *Nucleic Acids Res.* 8: 4057 (1980).

"Southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrocellulose, nylon, or another suitable membrane support for analysis with a radiolabeled, biotinylated or enzyme-labeled probe as described in sections 9.37–9.52 of Sambrook et al, supra.

"Northern analysis" is a method used to identify RNA sequences that hybridize to a known probe such as an oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Ligation" refers to the process of forming phosphodiester bonds between two nucleic acid fragments. To ligate the DNA fragments together, the ends of the DNA fragments must be compatible with each other. In some cases, the ends will be directly compatible after endonuclease digestion. However, it may be necessary to first convert the staggered ends commonly produced after endonuclease digestion to blunt ends to make them compatible for ligation. To blunt the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published 4 May 1988, or via deoxynucleoside H-phosphonate intermediates as described by Froehler et al., *Nucl. Acids Res.*, 14: 5399–5407 [1986]). They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich. ed., *PCR Technology*, (Stockton Press, N.Y., 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

II. SUITABLE METHODS FOR PRACTICING THE INVENTION

1. Preparation of Native PF4A Receptor and Variants

A. Isolation of DNA Encoding PF4A Receptor

The DNA encoding of the IL-8 and other PF4A receptors may be obtained from any cDNA library prepared from tissue believed to possess the PF4A receptor mRNA and to express it at a detectable level. The PF4A receptor gene may also be obtained from a genomic library. Libraries are screened with probes designed to identify the gene of interest or the protein encoded by it. We have described the entire cDNA for the IL-8 receptor. Nucleic acid encoding this receptor is readily obtained from genomic or neutrophil cDNA libraries using probes having oligonucleotide sequences from the IL-8 receptor gene set forth in FIGS. 2A–2I (SEQ ID NO:2). These probes usually will contain about 20 to 100 bases. Since the probes will hybridize perfectly to the IL-8 DNA, there is no need to use probe pools containing degenerate sequences. Screening with the probes is more efficient if performed under conditions of high stringency.

Other PF4A receptors are believed to contain regions of homology to the IL-8 receptor and thus probes having the sequences of the IL-8 receptor cDNA can be used to screen for these receptors as well. The best candidates for probes are those which represent sequences that are highly homologous among the human IL-8 receptor, the human fMLP receptor and the human C5a receptor (on the assumption that receptors of this class will all bear such regions), or which represent sequences that are highly divergent among such receptors (on the assumption that PF4A receptors as a class bear sites that are unique to the IL-8 receptor). IL-8 cDNA encoding the IL-8 residues 15–34, 78–94, 176–193, 264–282 and 299–312 will be useful. In general, one first identifies a cell which is capable of specifically binding or activated by a given PF4A, typically by in vitro bioassays and, optionally, by cell binding analysis using the labelled PF4A. Cells identified by this process (and some are already known for individual PF4As) therefore are expressing a receptor for this PF4A. A cDNA library is prepared from such cells and is screened using the IL-8 probes by procedures that are conventional per se. In this instance, however, it is preferred to use low stringency conditions and then analyze the resulting positive clones for homology to the IL-8 receptor. In general, candidate human PF4A receptors will exhibit greater than 75% amino acid sequence homology to the human IL-8 receptor and similar transmembrane loop structure. Assays are then conducted to confirm that hybridizing full length genes are the desired PF4A receptor.

The candidate is simply inserted into an expression vector and transformed into a host cell that ordinarily does not bind to the PF4A ligand. Transformants that acquire the ability to bind the ligand thus bear the desired receptor gene.

An alternative means to isolate genes encoding PF4A receptors other than the IL-8 receptor is to use polymerase chain reaction (PCR) methodology to amplify the target DNA or RNA, e.g. as described in section 14 of Sambrook et al., supra. This method requires the use of oligonucleotide probes that will hybridize to the PF4A receptor, and these readily are selected from the IL-8 receptor cDNA of FIGS. 2A–2I (SEQ ID NO:2). Strategies for selection of oligonucleotides are described below.

Another alternative method for obtaining the gene of interest is to chemically synthesize it using one of the methods described in Engels et al. (*Agnew. Chem. Int. Ed. Engl.*, 28: 716–734 [1989]), specifically incorporated by reference. These methods include triester, phosphite, phosphoramidite and H-Phosphonate methods. PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

A preferred method of practicing this invention is to use carefully selected oligonucleotide sequences to screen cDNA libraries from various tissues, preferably mammalian placental, fetal, brain, and carcinoma cell lines. More preferably, human or rabbit placental, fetal, brain, and carcinoma cell line cDNA libraries are screened with the oligonucleotide probes.

The oligonucleotide sequences selected as probes should be of sufficient length and sufficiently unambiguous that false positive are minimized. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labeling is to use 32-P labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the fact that PF4A receptors are not expressed with conventional signal sequences. Nucleic acid having the intact protein coding sequence is obtained by screening selected cDNA or genomic libraries, and, if necessary, using conventional primer extension procedures as described in section 7.79 of Sambrook et al., supra, to detect precursors and processing intermediates of mRNA that may not have been reverse-transcribed into cDNA. However, it is not necessary to seek DNAs encoding conventional signals.

B. Amino Acid Sequence Variants of the PF4A Receptor

Amino acid sequence variants PF4A receptor are prepared by introducing appropriate nucleotide changes into the PF4A receptor DNA, or by in vitro synthesis of the desired PF4A receptor polypeptide. Such variants include, for example, deletions from, or insertions or substitutions of, residues within the amino acid sequence shown for the human IL-8 receptor in FIGS. 2A–2I (SEQ ID NO:1). Any combination of deletion, insertion, and substitution can be made to arrive at the final construct, provided that the final construct possesses the desired characteristics. Excluded from the scope of this invention are PF4A receptor variants or polypeptide sequences that are not statutorily novel and unobvious over the prior art. The amino acid changes also may alter post-translational processes of the PF4A receptor, such as changing the number or position of glycosylation sites, altering the membrane anchoring characteristics, and/ or altering the intra-cellular location of the PF4A receptor by inserting, deleting, or otherwise affecting the leader sequence of the native PF4A receptor.

In designing amino acid sequence variants of PF4A receptors, the location of the mutation site and the nature of the mutation will depend on the PF4A receptor characteristic (s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1-3.

A useful method for identification of certain residues or regions of the PF4A receptor polypeptide that are preferred locations for mutagenesis is called "alanine scanning mutagenesis" as described by Cunningham and Wells (*Science*, 244: 1081-1085 [1989]). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed PF4A receptor variants are screened for the optimal combination of desired activity.

In general, the regions of the PF4A receptor molecule preferred for alterations are the regions that are not highly conserved. Such regions are those in which sequences of 5 or more residues are not conserved in the homologous position of the rabbit fMLP receptor. Amino acid sequence deletions generally range from about 1 to 30 residues, more preferably about 1 to 10 residues, and typically are contiguous. Deletions may be introduced into regions of low homology between the IL-8 receptor and the rabbit fMLP PF4A receptor to modify the activity of the IL-8 receptor. Deletions from the IL-8 receptor in areas of substantial homology with the rabbit fMLP receptors will be more likely to modify the biological activity of the IL-8 receptor more significantly. The number of consecutive deletions will be selected so as to preserve the tertiary structure of the PF4A receptor in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the PF4A receptor sequence) may range generally from about 1 to 10 residues, more preferably 1 to 5, most preferably 1 to 3.

Insertional variants of the PF4A receptor or its extracellular segments include the fusion to the N- or C-terminus of the PF4A receptor of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

Another group of variants are amino acid substitution variants. These variants have at least one amino acid residue in the PF4A receptor molecule removed and a different residue inserted in its place. The sites of greatest interest for substitutional mutagenesis include sites identified as the active site(s) of the PF4A receptor, and sites where the amino acids found in the PF4A receptor from various species are substantially different in terms of side-chain bulk, charge, and/or hydrophobicity.

Other sites of interest are those in which particular residues of the PF4A receptors obtained from various species are identical. These positions may the important for the biological activity of the PF4A receptor. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gin; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (N) | leu; phe.; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the PF4A receptor are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;

(5) residues that influence chain orientation: gly, pro; and (6) aromatic: trp, tyr, phe.

Non-conservative substitutions will entail exchanging a member of one of these classes for another. Such substituted residues may be introduced into regions of the PF4A receptor that are homologous with other PF4A receptors, or, more preferably, into the non-homologous regions of the molecule.

Any cysteine residues not involved in maintaining the proper conformation of the PF4A receptor may be substituted, generally with serine, to improve the oxidative stability of the molecule and prevent aberrant crosslinking.

DNA encoding amino acid sequence variants of the PF4A receptor is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the PF4A receptor. These techniques may utilized PF4A receptor nucleic acid (DNA or RNA), or nucleic acid complementary to the PF4A receptor nucleic acid.

Oligonucleotide-mediated mutagenesis is a preferred method for preparing substitution, deletion, and insertion variants of PF4A receptor DNA. This technique is well known in the art, for example as described by Adelman et al., *DNA*, 2: 183 (1983). Briefly, the PF4A receptor DNA is altered by hybridizing an oligonucleotide encoding the desired mutation to a DNA template, where the template is the single-stranded form of a plasmid or bacteriophage containing the unaltered or native DNA sequence of the PF4A receptor. After hybridization, a DNA polymerase is used to synthesize an entire second complementary strand of the template that will thus incorporate the oligonucleotide primer, and will code for the selected alteration in the PF4A receptor DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765 [1978]).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the PF4A receptor, and the other strand (the original template) encodes the native, unaltered sequence of the PF4A receptor. This heteroduplex molecule is then transformed into a suitable host cell, usually a prokaryote such as *E. coli* JM101. The cells are plated onto agarose plates, and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding PF4A receptor mutants with more than one amino acids to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of the PF4A receptor. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR. primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al. (*Gene*, 34: 315 [1985]). The starting material is the plasmid (or other vector) comprising the PF4A receptor DNA to be mutated. The codon(s) in the PF4A receptor DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the PF4A receptor DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated PF4A receptor DNA sequence.

C. Insertion of DNA into a Cloning Vehicle

The cDNA or genomic DNA encoding native or variant PF4A receptor is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the PF4A receptor DNA that is inserted into the vector. The native pro PF4A receptor DNA is directed to the cell surface, and in our recombinant cells, but it does not contain a conventional signal and no N-terminal polypeptide is cleaved during post-translational processing of the polypeptide to form the PF4A receptor.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the PF4A receptor DNA. However, the recovery of genomic DNA encoding the PF4A receptor is more complex than that of an exogenously replicated vector because restriction enzyme digestion is required to excise the PF4A receptor DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Appl. Genet.*, 1: 327 [1982]), mycophenolic acid (Mulligan et al., *Science*, 209: 1422 [1980]) or hygromycin (Sugden et al., *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the PF4A receptor nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the PF4A receptor. Amplification is the process by which genes in greater demand for the production of a protein critical for growth are reiterated in tandem within the chromosomes of successive generations of recombinant cells. Increased quantities of the PF4A receptor are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 [1980]. The transformed cells are then exposed to increased levels of methotrexate. This leads to the synthesis of multiple copies of the DHFR gene, and, concomitantly, multiple copies of other DNA comprising the expression vectors, such as the DNA encoding the PF4A receptor. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the PF4A receptor, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 [1979]; Kingsman et al., *Gene*, 7: 141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 85: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the PF4A receptor nucleic acid. Promoters are untranslated sequences located upstream (5') to the start codon of a structural gene (generally within about 100 to 1000 bp) that control the transcription and translation of a particular nucleic acid sequence, such as the PF4A receptor, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the PF4A receptor by removing the promoter from the source DNA by restriction enzyme digestion and inserting the isolated promoter sequence into the vector. Both the native PF4A receptor promoter sequence and many heterologous promoters may be used to direct amplification and/or expression of the PF4A receptor DNA. However, heterologous promoters are preferred, as they generally permit greater transcription and higher yields of expressed PF4A receptor as compared to the native PF4A receptor promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 20: 21–25 [1983]). However, other known bacterial promoters are suitable. Their nucleotide sequences have been published, thereby enabling a skilled worker operably to ligate them to DNA encoding the PF4A receptor (Siebenlist et al., *Cell*, 20: 269 [1980]) using linkers or adaptors to supply any required restriction sites. Promoters for use in bacterial systems also generally will contain a Shine-Dalgarno (S.D.) sequence operably linked to the DNA encoding the PF4A receptor.

Suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

PF4A receptor transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the PF4A receptor sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; Reyes et al., *Nature*, 297: 598–601 (1982) on expression of human β-interferon cDNA in mouse cells under the control of a thymidine kinase promoter from herpes simplex virus, Canaani and Berg, *Proc. Natl. Acad. Sci. USA*, 79: 5166–5170 (1982) on expression of the human interferon β1 gene in cultured mouse and rabbit cells, and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the PF4A receptor of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]) as well as within the coding sequence itself (Osborne et al., *Mol. Cell Bio.*, 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the PF4A receptor DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the PF4A receptor. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

Particularly useful in the practice of this invention are expression vectors that provide for the transient expression in mammalian cells of DNA encoding the PF4A receptor. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the PF4A receptor that have PF4A receptor-like activity.

Other methods, vectors, and host cells suitable for adaptation to the synthesis of the PF4A receptor in recombinant vertebrate cell culture are described in Gething et al., *Nature*, 293: 620–625 [1981]; Mantei et al., *Nature*, 281: 40–46 [1979]; Levinson et al.; EP 117,060; and EP 117,058. A particularly useful plasmid for mammalian cell culture expression of the PF4A receptor is pRK5 (EP pub. no. 307,247) or pSVI6B (U.S. Ser. No. 07/441,574 filed 22 Nov. 1989, the disclosure of which is incorporated herein by reference).

D. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aerupinosa*, *Salmonella typhimurium*, or *Serratia marcescens*. One preferred *E. coli* cloning host is *E. coli* 294 (ATCC 31,446), although other strains such as *E. coli* B, *E. coli* χ1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for vectors containing PF4A receptor DNA. *Saccharomyces cerevisiae*, or common baker's yeast, is the most commonly used among lower eukaryotic host microorganisms. However, a number of other genera, species, and strains are commonly available and useful herein, such as *S. pombe* [Beach and Nurse, *Nature*, 290: 140 (1981)], *Kluyveromyces lactis*

[Louvencourt et al., *J. Bacteriol.*, 737 (1983)], *yarrowia* [EP 402.226], *Pichia pastoris* [EP 183.070], *Trichoderma reesia* [EP 244.234], *Neurospora crassa* [Case et al., *Proc. Natl. Acad. Sci. USA*, 76: 5259–5263 (1979)], and *Aspergillus* hosts such as *A. nidulans* [Ballance at al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)] and *A. niger* [Kelly and Hynes, *EMBO J.*, 4: 475–479 (1985)].

Suitable host cells for the expression of glycosylated PF4A receptor polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the PF4A receptor DNA. During incubation of the plant cell culture with *A. tumefaciens*, the DNA encoding PF4A receptor is transferred to the plant cell host such that it is transfected, and will, under appropriate conditions, express the PF4A receptor DNA. In addition, regulatory and signal sequences compatible with plant cells are available, such as the nopaline synthase promoter and polyadenylation signal sequences. Depicker et al., *J. Mol. Appl. Gene*, 1: 561 (1982). In addition, DNA segments isolated from the upstream region of the T-DNA 780 gene are capable of activating or increasing transcription levels of plant-expressible genes in recombinant DNA-containing plant tissue. See EP 321.196 published 21 Jun. 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al. supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 Jun. 1989. For mammalian cells without such cell walls, the calcium phosphate precipitation method described in sections 16.30–16.37 of Sambrook et al. supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells such as by nuclear injection, electroporation, or by protoplast fusion may also be used.

E. Culturing the Host Cells

Prokaryotic cells used to produce the PF4A receptor polypeptide of this invention are cultured in suitable media as described generally in Sambrook et., al.

The mammalian host cells used to produce the PF4A receptor of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767.704; 4,657,866; 4,927,762; or 4,560,655; WO 90/03430; WO 87/00195; U.S. Pat. No. Re. 30,985; or copending U.S. Ser. No. 07/592,107 or 07/592,141, both filed in 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in vitro culture as well as cells that are within a host animal.

It is further envisioned that the PF4A receptor of this invention may be produced by homologous recombination, or with recombinant production methods utilizing control elements introduced into cells already containing DNA encoding the PF4A receptor. For example, a powerful promoter/enhancer element, a suppressor, or an exogenous transcription modulatory element is inserted in the genome of the intended host cell in proximity and orientation sufficient to influence the transcription of DNA encoding the desired PF4A receptor. The control element does not encode the PF4A receptor of this invention, but the DNA is present in the host cell genome. One next screens for cells making the PF4A receptor of this invention, or increased or decreased levels of expression, as desired.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/ or assay of sample fluids may be either monoclonal or polyclonal, and may be prepared in any mammal. Conveniently, the antibodies may be prepared against a native PF4A receptor polypeptide or against a synthetic peptide based on the DNA sequences provided herein as described further in Section 4 below.

G. Purification of The PF4A receptor Polypeptide

The PF4A receptor is recovered from the culture cells by solubilizing cell membrane in detergent.

When a human PF4A receptor is expressed in a recombinant cell other than one of human origin, the PF4A receptor is completely free of proteins or polypeptides of human origin. However, it is necessary to purify the PF4A receptor from recombinant cell proteins or polypeptides to obtain preparations that are substantially homogeneous as to the PF4A receptor. As a first step, the cells are centrifuged to separate them from culture medium. The membrane and soluble protein fractions are then separated. The PF4A receptor may then be purified from the membrane fraction of the culture lysate by solubilization with detergents followed by suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example. Sephadex G-75; hydrophobic affinity resins and ligand affinity using the appropriate PF4A immobilized on a matrix.

PF4A receptor variants in which residues have been deleted, inserted or substituted are recovered in the same fashion as the native PF4A receptor, taking account of any substantial changes in properties occasioned by the variation. For example, preparation of a PF4A receptor fusion with another protein or polypeptide, e.g. a bacterial or viral antigen, facilitates purification; an immunoaffinity column containing antibody to the antigen can be used to adsorb the fusion. Immunoaffinity columns such as a rabbit polyclonal anti-PF4A receptor column can be employed to absorb the PF4A receptor variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native PF4A receptor may require modification to account for changes in the character of the PF4A receptor or its variants upon expression in recombinant cell culture.

H. Covalent Modifications of PF4A receptor Polypeptides

Covalent modifications of PF4A receptor polypeptides are included within the scope of this invention. Both native PF4A receptors and amino acid sequence variants of the PF4A receptor may be covalently modified. One type of covalent modification included within the scope of this invention is a PF4A receptor polypeptide fragment. PF4A receptor fragments having up to about 40 amino acid residues may be conveniently prepared by chemical synthesis, or by enzymatic or chemical cleavage of the full-length PF4A receptor polypeptide or PF4A receptor variant polypeptide. Other types of covalent modifications of the PF4A receptor or fragments thereof are introduced into the molecule by reacting targeted amino acid residues of the PF4A receptor or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidazole)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high p; of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking PF4A receptor to a water-insoluble support matrix or surface for use in the method for purifying anti-PF4A receptor antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group.

Another type of covalent modification of the beta-8 polypeptide included within the scope of this invention comprises altering the native glycosylation pattern of the polypeptide. By altering is meant deleting one or more carbohydrate moieties found in the native receptor, and/or adding one or more glycosylation sites that are not present in the native receptor.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used. As noted above, the OL-8 receptor contains 6 putative N-linked glycosylation sites.

Addition of glycosylation sites to the PF4A receptor polypeptide is conveniently accomplished by altering the amino acid sequence such that it contains one or more of the above-described tri-peptide sequences (for N-linked glycosylation sites). The alteration may also be made by the addition of, or substitution by, one or more serine or threonine residues to the native PF4A receptor sequence (for O-linked glycosylation sites). For ease, the PF4A receptor amino acid sequence is preferably altered through changes at the DNA level, particularly by mutating the DNA encoding the PF4A receptor polypeptide at preselected bases such that codons are generated that will translate into the desired amino acids. The DNA mutation(s) may be made using methods described above under the heading of "Amino Acid Sequence Variants of PF4A receptor Polypeptide".

Another means of increasing the number of carbohydrate moieties on the beta-8 polypeptide is by chemical or enzymatic coupling of glycosides to the polypeptide. These procedures are advantageous in that they do not require production of the polypeptide in a host cell that has glycosylation capabilities for N- and O- linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston (*CRC Crit. Rev. Biochem., pp.* 259–306 [1981]).

Removal of carbohydrate moieties present on the native PF4A receptor polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin at al. (*Arch. Biochem. Biophys.*, 259:52 [1987]) and by Edge et al. (*Anal. Biochem.*, 118:131 [1981]). Enzymatic cleavage of carbohydrate moieties on polypeptides can be achieved by the use of a variety of endo- and exo- glycosidases as described by Thotakura et al. (*Meth, Enzymol.*, 138:350 [1987]).

Glycosylation at potential glycosylation sites may be prevented by the use of the compound tunicamycin as described by Duskin et al. (*J. Biol. Chem.*, 257:3105 [1982]). Tunicamycin blocks the formation of protein-N-glycoside linkages.

The PF4A receptor also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Osol, A., Ed., (1980).

PF4A receptor preparations are also useful in generating antibodies, for use as standards in assays for the PF4A receptor (e.g. by labeling the PF4A receptor for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant PF4A receptor, it will be appreciated that some screening of the recovered variant will be needed to select the optimal variant. For example, a change in the immunological character of the PF4A receptor molecule, such as affinity for a given antibody, is measured by a competitive-type immunoassay. The variant is assayed for changes in the suppression or enhancement of its activity by comparison to the activity observed for native PF4A receptor in the same assay. Other potential modifications of protein or polypeptide properties such as redox or thermal stability, hydrophobicity, susceptibility to proteolytic degradation, or the tendency to aggregate with carriers or into multimers are assayed by methods well known in the art.

3. Therapeutic Compositions and Administration of PF4A Receptor

Therapeutic formulations of PF4A receptor or its PF4A— binding fragments are prepared for storage by mixing PF4A receptor having the desired degree of purity with optional physiologically acceptable carriers, excipients, or stabilizers (*Remington's Pharmaceutical Sciences*, supra.), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The PF4A receptor or fragment to be used for in vivo administration must be sterile. This is readily accomplished by filtration through sterile filtration membranes, prior to or following lyophilization and reconstitution. The PF4A receptor ordinarily will be stored in lyophilized form or in solution.

Therapeutic PF4A receptor compositions generally are placed into a container having a sterile access port, for example, an intravenous solution bag or vial having a stopper pierceable by a hypodermic injection needle.

The route of PF4A receptor or PF4A receptor antibody administration is in accord with known methods, e.g. injection or infusion by intravenous, intraperitoneal, intracerebral, intramuscular, intraocular, intraarterial, or intralesional routes, or by sustained release systems as noted below. The PF4A receptor or fragment is administered continuously by infusion or by bolus injection. PF4A receptor antibody is administered in the same fashion, or by administration into the blood stream or lymph.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers*, 22: 547–556 [1983]), poly (2-hydroxyethylmethacrylate) (Langer et al., *J. Biomed. Mater. Res.*, 15: 167– 277 [1981] and Langer, *Chem. Tech.*, 12: 98–105 [1982]), ethylene vinyl acetate (Langer et al., supra) or poly-D-(-)-3-hydroxybutyric acid (EP 133,988). Sustained-release PF4A receptor compositions also include liposomally entrapped PF4A receptor. Liposomes containing PF4A receptor are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal PF4A receptor therapy.

An effective amount of PF4A receptor to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the PF4A receptor or fragment until a dosage is reached that achieves the desired effect. The progress of this therapy is easily monitored by conventional assays.

4. PF4A receptor Antibody Preparation

Polyclonal antibodies to the PF4A receptor generally are raised in animals by multiple subcutaneous (sc) or intraperitoneal (ip) injections of the PF4A receptor and an adjuvant. It may be useful to conjugate the PF4A receptor or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals ordinarily are immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's incomplete adjuvant by subcutaneous injection at multiple sites. 7 to 14 days later animals are bled and the serum is assayed for anti-PF-4A receptor titer. Animals are boosted until the titer plateaus. Preferably, the animal is boosted with the conjugate of the same PF4A receptor, but conjugated to a different protein and/or through a different cross-linking agent. Conjugates also can be made in recombinant cell culture as protein fusions. Also, aggregating agents such as alum are used to enhance the immune response. It may be convenient to immunize the animal with an analogous host cell which has been transformed to express the target receptor of another species.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The monoclonal antibody preferably does not cross-react with other known PF4A receptor polypeptides.

5. Uses of PF4A Receptor and its Antibodies

The nucleic acid encoding the PF4A receptor may be used as a diagnostic for tissue specific typing. For example, such procedures as in situ hybridization, and northern and Southern blotting, and PCR analysis may be used to determine whether DNA and/or RNA encoding the PF4A receptor are present in the cell type(s) being evaluated.

Isolated PF4A receptor polypeptide may be used in quantitative diagnostic assays as a standard or control against which samples containing unknown quantities of PF4A receptor may be compared. Recombinant cells which express the receptor can be used in assays for PF4A ligands in the same fashion as for example neutrophils are used in IL-8 assays.

PF4A receptor antibodies are useful in diagnostic assays for PF4A receptor expression in specific cells or tissues. The antibodies are labeled in the same fashion as the PF4A receptor described above and/or are immobilized on an insoluble matrix.

PF4A receptor antibodies also are useful for the affinity purification of the PF4A receptor from recombinant cell culture or natural sources. The PF4A receptor antibodies that do not detectably cross-react with other PF4A receptors can be used to purify each PF4A receptor free from other known receptors of the class.

Suitable diagnostic assays for the PF4A receptor and its antibodies are well known per se. Such assays include competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of the PF4A receptor and for substances that bind the PF4A receptor, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for the PF4A receptor or its antibodies all use one or more of the following reagents: labeled analyte analogue, immobilized analyte analogue, labeled binding partner, immobilized binding partner and steric conjugates. The labeled reagents also are known as "tracers."The label used (and this is also useful to label PF4A receptor nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, New York, 1981), pp. 147–166. Such bonding methods are suitable for use with PF4A receptor or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the PF4A receptor or its immunologically active fragments are conjugated with a bifunctional organic bridge to an enzyme such as peroxidase. Conjugates are selected for use with anti-PF4A receptor so that binding of the anti-PF4A receptor inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of PF4A receptor or PF4A receptor antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-PF4A receptor monoclonal antibody as one antibody and a polyclonal anti-PF4A receptor antibody as the other is useful in testing samples for PF4A receptor activity.

The foregoing are merely exemplary diagnostic assays for PF4A receptor and antibodies. Other methods now or hereafter developed for the determination of these analytes are included within the scope hereof, including the bioassays described above.

All references cited in this specification are expressly incorporated by reference.

The following examples are offered by way of illustration and not by way of limitation.

EXAMPLE 1

To obtain the clone pRK5B.il8r1.1, a cDNA[16] library of 1,000,000 clones was constructed from human neutrophil mRNA[17] in the vector pRK5B using bstXI linkers. The cDNA is produced in blunted form. Hemi-kinase bstXI linkers are ligated to the CDNA, and the linkers ligated into the PRK5B vector that had been bstXI digested, phosphatased, and the long vector fragment isolated. PRK5B is a derivative of PRK5[18] that contains a cytomegalovirus promoter followed by a 5' intron, bstXI cloning site, and an SV40 early polyadenylation signal, although it will be understood that any mammalian cell expression vector will be satisfactory. 58 pools of 2500 clones each were transfected into COS-7 cells by electroporation[19] of 20 µg of DNA into 3,750,000 cells After 2 days of growth on 150-mm dishes in medium (50:50::Ham's F12:DMEM) containing 10% fetal calf serum, $^{125}$I-IL-8 binding was performed. Purified human 72 amino acid IL-8 made in *E. coli*[20] was labeled by the lactoperoxidase method[21] to about 1100 Ci/mmol and was at least 85% bindable. Dishes were rinsed twice with phosphate-buffered saline, and binding was performed with 8 ml per dish of growth medium containing 2.5% fetal calf serum and about 0.5 nM $^{125}$I-IL-8. After 2 hr at 37°, the plates were rinsed three times with phosphate-buffered saline, the bottoms cut out[22], and autoradiographed. Each positive pool of 2500 cDNA clones was subsequently partitioned into pools of 800 clones, and each of these was transfected and assayed. Each positive pool in turn was subdivided through pools of 185, 30 and finally a single clone(s) until single positive clones were identified to obtain the pure isolate. Since only a portion of each pool was used for transfection it was unnecessary to rescue clones from transformants.

Binding competition was performed with electroporated COS-7 cells after 1 day of expression in 6-well dishes (about 175,000 cells/dish). Binding was performed with radioiodinated wild type IL-8 in binding medium $Ca^{2+}$ and $Mg^{2+}$-free Hanks buffered with 25 nM Hepes and supplemented with 0.5% BSA) at 4° for about 2 hr. Wells were then washed, the cells harvested with trypsin, and counted. No specific binding was found in parallel wells containing cells transfected with DNA from the vector pRK5B. Neutrophil binding was performed as described[22] but for 2 hr at 4°.

REFERENCES

1. Oppenheim, J. J. et al. *Annu. Rev. Immunol.* 9, 617–648 (1991).
2. Gimbrone, M. A. Jr. et al. *Science* 246, 1601–3 (1989).
3. Boulay, F. et al. *Biochem. Biophys. Res. Comm.* 168, 1103–1109 (1990).
4. Gerard, N. P. & Gerard, C. *Nature*, 349, 614–617 (1991).
5. Thomas, K. M., Pyun, H. Y. & Navarro, J. *J . Biol. Chem.* 265, 20061–20064 (1990).
6. Sims, J. E. et al. *Science*, 241, 585–589 (1988).
7. D'Andrea, A. D., Lodish, H. F. & Wong, G. G. *Cell*, 57, 277–285 (1989).
8. Samanta, A. K., Oppenheim, J. J. & Matsushima, K. *J. Exp. Med.* 169, 1185–1189 (1989).
9. Besemer, J., Hujber, A. & Kuhn, B. *J. Biol. Chem.* 264, 17409–17415 (1989).
10. Grob, P. M. et al. *J. Biol. Chem.* 265, 8311–8316 (1990).
11. Kozak, M., *Nucleic Acid Res.* 12, 857–872 (1984).
12. Dixon, R. A. F., Sigal, I. S. & Strader, C. D. *Cold Spring Har. Sym. Quant. Biol.*, 53, 487–497 (1988).
13. Korchak, H. M. et al. *J. Biol Chem.*, 259, 4076–4082 (1984).
14. Tennenberg, S. D., Zemlan, F. P. & Solomkin J. S. *J. Immunol.*, 141, 3937–3944 (1988).
15. Ramachandran, J. et al. *BioEssays*, 10, 54–57 (1989).
16. Gubler, U. & Hoffman, B. J. *Gene*, 25, 263–269, (1983).
17. Chirgwin, J. J et al. *Biochem.*, 18, 5294–5299 (1979)
18. EP 307,247
19. Gearing, D. P. et al. *EMBO J.*, 8, 3667–3676 (1989).
20. Hebert, C. A. et al. *J. Immunol.*, 145:3033–3040 (1991).
21. Morrison M. & Bayse, G. S. *Biochem.* 9, 2995–3000 (1970)
22. Pacholczyk, T., Blakely, R. D. & Amara, S. G., *BioTechniques*, 9, 556–558 (1990).
23. Grynkiewicz, G., Poenie, M. & Tsien, R. Y. *J. Biol. Chem.*, 260, 3440–3450 (1985).

We claim:

1. An isolated PF4A receptor polypeptide comprising the N-terminal extracellular region contained in the human IL-8 receptor polypeptide amino acid sequence of SEQ ID NO:1.

2. The PF4A receptor polypeptide of claim 1 that comprises the human IL-8 receptor polypeptide amino acid sequence of SEQ ID NO:1.

3. A composition comprising the PF4A receptor polypeptide of claim 1 and a pharmaceutically acceptable carrier.

4. The composition of claim 3 which is essentially free of other cell membrane proteins.

5. An isolated polypeptide comprising the PF4A receptor polypeptide of claim 1 fused to a polypeptide heterologous to the receptor.

6. An antibody that binds the human IL-8 receptor polypeptide amino acid sequence of SEQ ID NO:1.

7. The antibody of claim 6 that is a monoclonal antibody.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 350 amino acids
        ( B ) TYPE: Amino Acid
        ( D ) TOPOLOGY: Linear ( x i ) SEQUENCE DESCRIPTION: SEQ ID NO:1:

```
Met  Ser  Asn  Ile  Thr  Asp  Pro  Gln  Met  Trp  Asp  Phe  Asp  Asp  Leu
 1              5                   10                            15

Asn  Phe  Thr  Gly  Met  Pro  Pro  Ala  Asp  Glu  Asp  Tyr  Ser  Pro  Cys
                     20                   25                           30

Met  Leu  Glu  Thr  Glu  Thr  Leu  Asn  Lys  Tyr  Val  Val  Ile  Ile  Ala
                     35                   40                           45

Tyr  Ala  Leu  Val  Phe  Leu  Leu  Ser  Leu  Leu  Gly  Asn  Ser  Leu  Val
                     50                   55                           60

Met  Leu  Val  Ile  Leu  Tyr  Ser  Arg  Val  Gly  Arg  Ser  Val  Thr  Asp
                     65                   70                           75

Val  Tyr  Leu  Leu  Asn  Leu  Ala  Leu  Ala  Asp  Leu  Leu  Phe  Ala  Leu
                     80                   85                           90

Thr  Leu  Pro  Ile  Trp  Ala  Ala  Ser  Lys  Val  Asn  Gly  Trp  Ile  Phe
                     95                  100                          105

Gly  Thr  Phe  Leu  Cys  Lys  Val  Val  Ser  Leu  Leu  Lys  Glu  Val  Asn
                    110                  115                          120

Phe  Tyr  Ser  Gly  Ile  Leu  Leu  Leu  Ala  Cys  Ile  Ser  Val  Asp  Arg
                    125                  130                          135

Tyr  Leu  Ala  Ile  Val  His  Ala  Thr  Arg  Thr  Leu  Thr  Gln  Lys  Arg
                    140                  145                          150

His  Leu  Val  Lys  Phe  Val  Cys  Leu  Gly  Cys  Trp  Gly  Leu  Ser  Met
                    155                  160                          165

Asn  Leu  Ser  Leu  Pro  Phe  Phe  Leu  Phe  Arg  Gln  Ala  Tyr  His  Pro
                    170                  175                          180

Asn  Asn  Ser  Ser  Pro  Val  Cys  Tyr  Glu  Val  Leu  Gly  Asn  Asp  Thr
                    185                  190                          195

Ala  Lys  Trp  Arg  Met  Val  Leu  Arg  Ile  Leu  Pro  His  Thr  Phe  Gly
                    200                  205                          210

Phe  Ile  Val  Pro  Leu  Phe  Val  Met  Leu  Phe  Cys  Tyr  Gly  Phe  Thr
                    215                  220                          225

Leu  Arg  Thr  Leu  Phe  Lys  Ala  His  Met  Gly  Gln  Lys  His  Arg  Ala
                    230                  235                          240

Met  Arg  Val  Ile  Phe  Ala  Val  Val  Leu  Ile  Phe  Leu  Leu  Cys  Trp
                    245                  250                          255

Leu  Pro  Tyr  Asn  Leu  Val  Leu  Leu  Ala  Asp  Thr  Leu  Met  Arg  Thr
                    260                  265                          270

Gln  Val  Ile  Gln  Glu  Thr  Cys  Glu  Arg  Arg  Asn  Asn  Ile  Gly  Arg
                    275                  280                          285

Ala  Leu  Asp  Ala  Thr  Glu  Ile  Leu  Gly  Phe  Leu  His  Ser  Cys  Leu
                    290                  295                          300

Asn  Pro  Ile  Ile  Tyr  Ala  Phe  Ile  Gly  Gln  Asn  Phe  Arg  His  Gly
                    305                  310                          315
```

| Phe | Leu | Lys | Ile | Leu | Ala | Met | His | Gly | Leu | Val | Ser | Lys | Glu | Phe |
|-----|-----|-----|-----|-----|-----|-----|-----|-----|-----|-----|-----|-----|-----|-----|
|     |     |     |     | 320 |     |     |     |     | 325 |     |     |     |     | 330 |

| Leu | Ala | Arg | His | Arg | Val | Thr | Ser | Tyr | Thr | Ser | Ser | Ser | Val | Asn |
|-----|-----|-----|-----|-----|-----|-----|-----|-----|-----|-----|-----|-----|-----|-----|
|     |     |     |     | 335 |     |     |     |     | 340 |     |     |     |     | 345 |

| Val | Ser | Ser | Asn | Leu |
|-----|-----|-----|-----|-----|
|     |     |     |     | 350 |

( 2 ) INFORMATION FOR SEQ ID NO:2:

( i ) SEQUENCE CHARACTERISTICS:
( A ) LENGTH: 1933 base pairs
( B ) TYPE: Nucleic Acid
( C ) STRANDEDNESS: Single
( D ) TOPOLOGY: Linear ( x i ) SEQUENCE DESCRIPTION: SEQ ID NO:2:

| | | | | | |
|---|---|---|---|---|---|
| CCTGGCCGGT | GCTTCAGTTA | GATCAAACCA | TTGCTGAAAC | TGAAGAGGAC | 50 |
| ATGTCAAATA | TTACAGATCC | ACAGATGTGG | GATTTTGATG | ATCTAAATTT | 100 |
| CACTGGCATG | CCACCTGCAG | ATGAAGATTA | CAGCCCCTGT | ATGCTAGAAA | 150 |
| CTGAGACACT | CAACAAGTAT | GTTGTGATCA | TCGCCTATGC | CCTAGTGTTC | 200 |
| CTGCTGAGCC | TGCTGGGAAA | CTCCCTGGTG | ATGCTGGTCA | TCTTATACAG | 250 |
| CAGGGTCGGC | CGCTCCGTCA | CTGATGTCTA | CCTGCTGAAC | CTGGCCTTGG | 300 |
| CCGACCTACT | CTTTGCCCTG | ACCTTGCCCA | TCTGGGCCGC | CTCCAAGGTG | 350 |
| AATGGCTGGA | TTTTTGGCAC | ATTCCTGTGC | AAGGTGGTCT | CACTCCTGAA | 400 |
| GGAAGTCAAC | TTCTACAGTG | GCATCCTGCT | GTTGGCCTGC | ATCAGTGTGG | 450 |
| ACCGTTACCT | GGCCATTGTC | CATGCCACAC | GCACACTGAC | CCAGAAGCGT | 500 |
| CACTTGGTCA | AGTTTGTTTG | TCTTGGCTGC | TGGGGACTGT | CTATGAATCT | 550 |
| GTCCCTGCCC | TTCTTCCTTT | TCCGCCAGGC | TTACCATCCA | AACAATTCCA | 600 |
| GTCCAGTTTG | CTATGAGGTC | CTGGGAAATG | ACACAGCAAA | ATGGCGGATG | 650 |
| GTGTTGCGGA | TCCTGCCTCA | CACCTTTGGC | TTCATCGTGC | CGCTGTTTGT | 700 |
| CATGCTGTTC | TGCTATGGAT | TCACCCTGCG | TACACTGTTT | AAGGCCCACA | 750 |
| TGGGGCAGAA | GCACCGAGCC | ATGAGGGTCA | TCTTTGCTGT | CGTCCTCATC | 800 |
| TTCCTGCTTT | GCTGGCTGCC | CTACAACCTG | GTCCTGCTGG | CAGACACCCT | 850 |
| CATGAGGACC | CAGGTGATCC | AGGAGACCTG | TGAGCGCCGC | AACAACATCG | 900 |
| GCCGGGCCCT | GGATGCCACT | GAGATTCTGG | GATTTCTCCA | TAGCTGCCTC | 950 |
| AACCCCATCA | TCTACGCCTT | CATCGGCCAA | AATTTTCGCC | ATGGATTCCT | 1000 |
| CAAGATCCTG | GCTATGCATG | GCCTGGTCAG | CAAGGAGTTC | TTGGCACGTC | 1050 |
| ATCGTGTTAC | CTCCTACACT | TCTTCGTCTG | TCAATGTCTC | TTCCAACCTC | 1100 |
| TGAAAACCAT | CGATGAAGGA | ATATCTCTTC | TCAGAAGGAA | AGAATAACCA | 1150 |
| ACACCCTGAG | GTTGTGTGTG | GAAGGTGATC | TGGCTCTGGA | CAGGCACTAT | 1200 |
| CTGGGTTTTG | GGGGACGCT | ATAGGATGTG | GGGAAGTTAG | GAACTGGTGT | 1250 |
| CTTCAGGGGC | CACACCAACC | TTCTGAGGAG | CTGTTGAGGT | ACCTCCAAGG | 1300 |
| ACCGGCCTTT | GCACCTCCAT | GGAAACGAAG | CACCATCATT | CCCGTTGAAC | 1350 |
| GTCACATCTT | TAACCCACTA | ACTGGCTAAT | TAGCATGGCC | ACATCTGAGC | 1400 |
| CCCGAATCTG | ACATTAGATG | AGAGAACAGG | GCTGAAGCTG | TGTCCTCATG | 1450 |
| AGGGCTGGAT | GCTCTCGTTG | ACCCTCACAG | GAGCATCTCC | TCAACTCTGA | 1500 |

-continued

| | | | | | |
|---|---|---|---|---|---|
| GTGTTAAGCG | TTGAGCCACC | AAGCTGGTGG | CTCTGTGTGC | TCTGATCCGA | 1550 |
| GCTCAGGGGG | GTGGTTTTCC | CATCTCAGGT | GTGTTGCAGT | GTCTGCTGGA | 1600 |
| GACATTGAGG | CAGGCACTGC | CAAAACATCA | ACCTGCCAGC | TGGCCTTGTG | 1650 |
| AGGAGCTGGA | AACACATGTT | CCCCTTGGGG | GTGGTGGATG | AACAAAGAGA | 1700 |
| AAGAGGGTTT | GGAAGCCAGA | TCTATGCCAC | AAGAACCCCC | TTTACCCCCA | 1750 |
| TGACCAACAT | CGCAGACACA | TGTGCTGGCC | ACCTGCTGAG | CCCCAAGTGG | 1800 |
| AACGAGACAA | GCAGCCCTTA | GCCCTTCCCC | TCTGCAGCTT | CCAGGCTGGC | 1850 |
| GTGCAGCATC | AGCATCCCTA | GAAAGCCATG | TGCAGCCACC | AGTCCATTGG | 1900 |
| GCAGGCAGAT | GTTCCTAATA | AAGCTTCTGT | TCC | | 1933 |